(12) United States Patent
Shemer et al.

(10) Patent No.: US 8,922,777 B2
(45) Date of Patent: Dec. 30, 2014

(54) OPTICAL DENSITY SENSOR CALIBRATION AND SELF FIXING

(75) Inventors: Zvi Shemer, Nes Ziona (IL); Ziv Gilan, Kfar-Harif (IL); Niv Shemtov, Rishon Letzion (IL); Shlomo Harush, Nes-Ziona (IL); Natty Levy, Raanana (IL); Amit Porat, Rehovot (IL)

(73) Assignee: Hewlett-Packard Development Company, L.P., Houston, TX (US)

( * ) Notice: Subject to any disclaimer, the term of this patent is extended or adjusted under 35 U.S.C. 154(b) by 754 days.

(21) Appl. No.: 13/160,088

(22) Filed: Jun. 14, 2011

(65) Prior Publication Data

US 2012/0320378 A1    Dec. 20, 2012

(51) Int. Cl.
| | | |
|---|---|---|
| *G01N 21/00* | (2006.01) | |
| *G09G 3/34* | (2006.01) | |
| *G09G 1/06* | (2006.01) | |
| *G01D 18/00* | (2006.01) | |
| *G01D 21/00* | (2006.01) | |
| *G01N 21/59* | (2006.01) | |
| *G01N 21/27* | (2006.01) | |

(52) U.S. Cl.
CPC .......... *G01N 21/274* (2013.01); *G01N 21/5907* (2013.01)
USPC ............... 356/434; 356/436; 345/84; 345/19; 702/85

(58) Field of Classification Search
CPC  G01B 21/274; G01B 21/5907; B41J 2/17596
USPC ................ 137/265, 571; 347/6, 7, 19, 84, 85; 356/434, 432, 445, 448, 402, 408; 702/85, 134
See application file for complete search history.

(56) References Cited

U.S. PATENT DOCUMENTS

| | | | |
|---|---|---|---|
| 4,862,192 A * | 8/1989 | Slomianny | 347/7 |
| 6,055,011 A | 4/2000 | Nishimura | |
| 6,418,281 B1 | 7/2002 | Ohki | |
| 6,663,220 B2 * | 12/2003 | Suzuki et al. | 347/36 |
| 7,293,849 B2 * | 11/2007 | Tani et al. | 347/6 |
| 2004/0189742 A1 * | 9/2004 | Kimura et al. | 347/33 |
| 2005/0264619 A1 * | 12/2005 | Walton et al. | 347/84 |
| 2006/0087539 A1 * | 4/2006 | Loyd et al. | 347/89 |
| 2008/0226316 A1 | 9/2008 | Koshimura et al. | |
| 2009/0080920 A1 | 3/2009 | Carter et al. | |
| 2010/0225715 A1 * | 9/2010 | Bachar et al. | 347/86 |
| 2012/0299989 A1 * | 11/2012 | Prothon et al. | 347/6 |

FOREIGN PATENT DOCUMENTS

JP         2006267895 A    10/2006

* cited by examiner

*Primary Examiner* — Kara A Geisel
*Assistant Examiner* — Dominic J Bologna (57) ABSTRACT

A method of calibrating an optical density sensor comprising calculating a first pigment solid density value of an ink solution using a current first electrical output signal value from a photodetector, a current second electrical output signal value from a photodetector, and a current lens gap value, calculating a second pigment solid density value of the ink solution using a previously measured first electrical output signal value, a previously measured second electrical output signal value, and a previously measured lens gap value, comparing the current first electrical output signal value, the current second electrical output signal value, and the current lens gap value with the previously measured first electrical output signal value, the previously measure second electrical output signal value, and the previously measured lens gap value, and comparing the first pigment solid density value with the second pigment solid density value.

20 Claims, 6 Drawing Sheets

OPTICAL DENSITY SENSOR CALIBRATION AND SELF FIXING

BACKGROUND

One issue effecting print quality is the ability to accurately measure the pigment density within an ink solution. Accurate and consistent pigment density within the ink solution results in a more appealing printed product. In order to achieve accurate and consistent pigment density throughout the supply of ink within a printing device, an optical density sensor may be used.

BRIEF DESCRIPTION OF THE DRAWINGS

The accompanying drawings illustrate various examples of the principles described herein and are a part of the specification. The illustrated examples do not limit the scope of the claims.

Throughout the drawings, identical reference numbers designate similar, but not necessarily identical, elements.

DETAILED DESCRIPTION

An optical density sensor uses a light source, a number of lenses and a photodetector to determine the ink pigment density of an ink solution. In order to measure the pigment density, the optical density sensor may pass an amount of ink in between a light source and a photodetector. The individual pigment particles within the ink, when passed through the light and in between a number of lenses, either absorb or reflect the light from the light source. Consequently, this prevents at least a portion of the light from reaching the photodetector. The light that is not blocked is able to reach the photodetector and the amount of light is measured by the photodetector. Through this process, the particle density of the ink may then be calculated.

However, the sensitive electrical and mechanical components of the optical density sensors may be unintentionally worn down or even damaged. The damage may be brought about during the fabrication process of the printing system or during normal operation of the sensor after purchase. A worn down or damaged optical density sensor will not be able to provide accurate or precise density readings. Additionally, each individual sensor will be more or less independently susceptible to any type of damage and will produce a myriad of different results among the different sensors.

During manufacturing, assembly, packaging, transportation, and general use of each optical density sensor, the components of the optical density sensor may be altered significantly enough to require calibration of the sensor. One example of a component that may be affected by the above circumstances is the lenses within the sensor. Alignment of the lenses within the sensor may be altered resulting in a wide variety of differing results between individual sensors. Additionally, when the ink solution passes between the lenses of the photodetector, the ink solution may form a film over the lenses that may also distort the sensors' results. Other environmental factors such as ageing of the electrical parts of the optical density sensor may add to or result in skewed or incorrect results while measuring the particle density within a sample of ink.

In order to overcome the issues mentioned above, the optical density sensor may be calibrated. One way to accomplish this calibration may be to generate, experimentally, an average look-up table containing the averaged rates of density to light intensity values at a given set point. The calibration process for all optical density sensors may then be performed using the one averaged set point. However, this process has a number of disadvantages. Specifically, when implementing the process, it is assumed that for little changes in the particle density of the ink, the influence on intensity is linear around that averaged set point. Additionally, with this process, it is assumed that the changes in the light intensity value measured by the optical density sensor are the same for each optical density sensor. Still further, with this process, it is assumed that every optical density sensor has the same gap distance between the lenses used within the optical density sensor and if it isn't the same, it is at least averaged.

As a result of these assumptions, the above process provides accurate light intensity values to a certain degree relatively close to the set point. For significantly larger or smaller density values, however, the accuracy of the measurements begins to drop. Indeed, in connection with the above process, and referring the set point as 100%, with a difference in 2% pigment density from the set point, the inaccuracy may reach as high as 1% pigment density. However, moving even further from the set point, for example 33%, may produce an inaccuracy in pigment density as high as 20%. Using the above method, therefore, results in a system that produces printed products that will not appear optimal.

Still further, in using this process there would be no way of recognizing any electrical or mechanical failures within the optical density sensor itself. Therefore, the user of the optical density sensor would not know if and how to appropriately recalibrate, repair or replace the optical density sensor.

The present specification therefore describes a method and system for calibrating and troubleshooting an optical density sensor. Specifically the present specification describes a method and system for calibrating and troubleshooting an optical density sensor by taking intensity values of a laser beam that pass through an ink solution having a specific pigment density; a portion of the intensity being absorbed by the ink solution, calculating the ink density of the ink solution at that specific pigment density, calculating the lens gap, and comparing these values with new ink density measurements taken with the sensor during an ink building process. The optical density sensor may then be recalibrated based on the new measurements. Additionally, the user may be alerted if the new measurements have indicated that the optical density sensor has relatively more serious issues such as internal mechanical or electrical issues. A troubleshooting process may then be initiated to determine what part or parts of the optical density sensor are having issues and whether these parts need to be repaired or replaced.

In the present specification and in the appended claims, the terms "calibrate" or "recalibrate" are meant to be understood broadly as the process through which any deviation in measurements of an optical density sensor are detected, corrected, and rectified. In one example, an optical density sensor may be calibrated so that, during an ink building procedure, the proper amount of pigment solids may be included in an ink solution thereby resulting in an accurate pigment solid density within the ink solution.

Additionally, in the present specification and in the appended claims, the term "density" is meant to be understood as the mass of a substance per unit of weight. In some examples, the density refers to the amount of pigment solids within an ink solution. Still further, the terms "pigment concentration" or "percent of non-evaporated solids (% NVS)" is also meant to be understood broadly as the amount of pigment solids within an ink solution.

Still further, in the present specification an in the appended claims, the terms "light" or "electromagnetic energy" is meant to be understood as broadly as In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language means that a particular feature, structure, or characteristic described in connection with that example is included as described, but may not be included in other examples.

Figure 1:
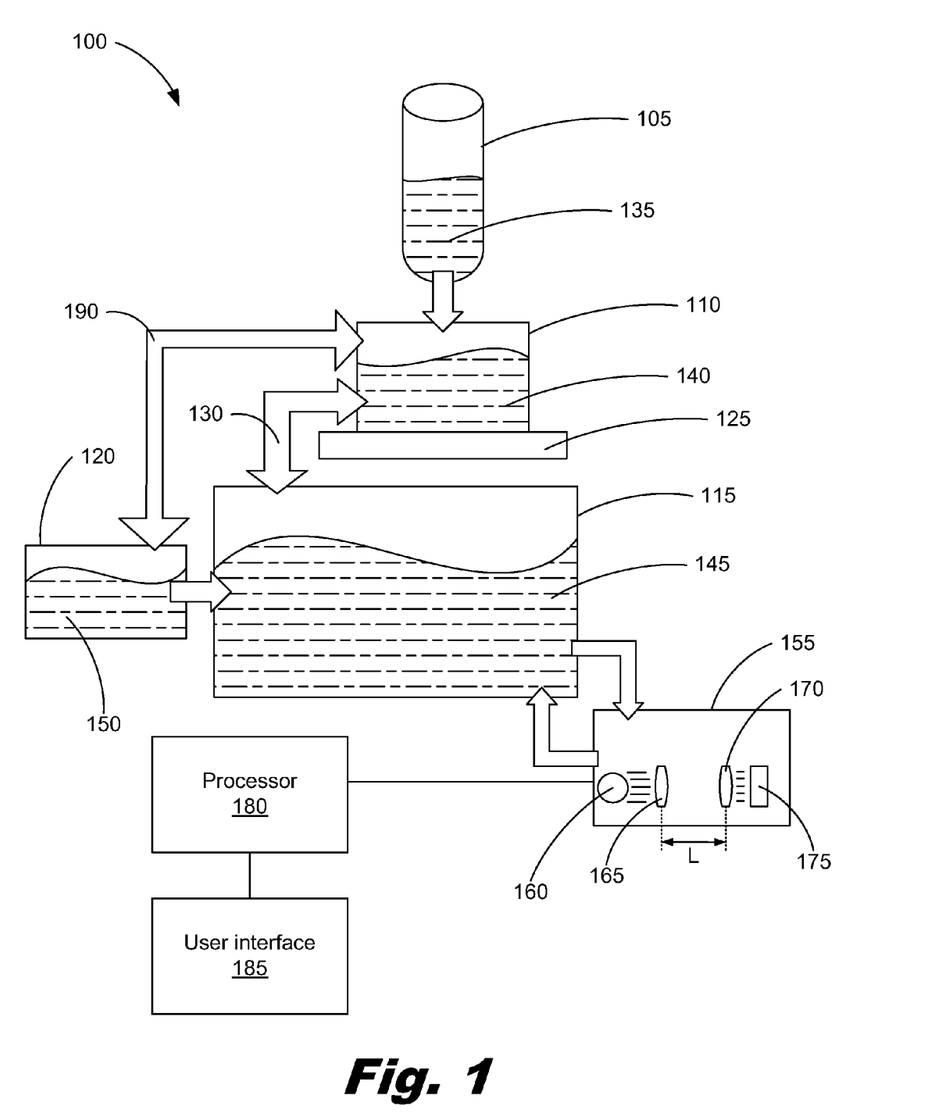
FIG. 1 is a diagram of an ink building system within a printer according to one example of principles described herein.

Turning now to FIG. 1, a diagram of an ink building system (100) within a printer is shown according to one example of principles described herein. The system (100) may include an ink calibration can (105), an intermediate dispersion unit (110), an ink tank (115), a base oil tank (120), a load cell (125), a first pump (130), a second pump (190), and an optical density sensor (155). As will be described in more detail below, the ink calibration can (105) may contain pigment solids (135); the intermediate dispersion unit (110) may contain at times an amount of oil (150) and pigment solids (135) making up a first ink solution (140); and, the ink tank (115) may contain an amount of oil (150) and pigment (135) making up a second ink solution (145). The first (140) and second (145) ink solutions may contain varying densities of pigment solids (135) at different times. Additionally, the system (100) may further comprise a processor (180) and user interface (185) which, as will be described below, allows a user to interact with the system (100). The above elements will now be described in more detail.

The calibration can (105), as mentioned above, may contain an amount of pigment solids (135) that are to be combined with a base component of the ink, such as oil (150), within the intermediate dispersion unit (110). Because the type of pigment solids (135) used determines the final color of the ink to be used in the system (100), many calibration cans (105) may be used. Each calibration can (105) may contain a specific type of pigment (135) that would produce a certain color of ink when added to an oil (150). However for simplicity in illustration, one calibration can (105) and one type of pigment solid (135) is shown in FIG. 1. Additionally, for simplicity in illustration the pigment solid (135) used in the example shown in FIG. 1 is black.

The intermediate dispersion unit (110) serves as a buffer tank that allows oil (150) to be mixed with pigment solids (135). The intermediate dispersion unit (110) may also serve to allow additional pigment solids (135) to be mixed with an ink containing an established amount or density of pigment solids (135). As will be discussed below, the intermediate dispersion unit (110) may, therefore, be used to incrementally increase the pigment density of the second ink solution (145) kept within the tank (115) in order to achieve a desired pigment density level. At the factory, initial calibration of the optical density sensor may be accomplished through the use of a load cell (125). The load cell (125) measures the weight of any pigment solids (135) added to the intermediate dispersion unit (110).

As mentioned above, the ink tank (115) may also contain an ink comprising varying densities of pigment solids (135) at various times. The tank (115) may be fluidly coupled to both the intermediate dispersion unit (110) and a base oil tank (120). Fluidly coupling the ink tank (115) to the base oil tank (120) may be done so that inks containing varying pigment solid (135) densities may be mixed with an amount of oil (150) from the base oil tank (120) and stored, at least temporarily, in the ink tank (115). Fluidly coupling the ink tank (115) to the intermediate dispersion unit (110) allows at least a portion of the second ink solution (145) to be pumped into the intermediate dispersion unit (110) so that additional pigment solids (135) may be added to the second ink solution (145). The ink tank (115) may also serve as the reservoir from which the printing system (100) may retrieve an additional amount of ink solution for printing.

The second ink solution (145) discussed above may be pumped into the intermediate dispersion unit (110) via the first pump (130). The first pump (130) may also pump at least a portion of the first ink solution (140) into the ink tank (115). Still further, the first pump (130) may pump the second ink solution (145) back into the ink tank (115) after an additional amount of pigment solids (135) has been added to the second ink solution (145).

In another example, a second pump (190) may fluidly couple the base oil tank (120) directly to the intermediate dispersion unit (110). Fluidly coupling the base oil tank (120) to the intermediate dispersion unit (110) via the second pump (190) may allow additional amounts of oil (150) to be added to the ink solution (140, 145) during the ink building process described above.

The ink tank (115) may also be fluidly coupled to an optical density sensor (155). The optical density sensor (155) periodically tests the pigment (135) density within the second ink solution (145) so that the optimal predetermined density level may be obtained. As will be discussed later, the optical density sensor (155) may test the pigment solid (135) density of the second ink solution (145) after an ink solution has been received into the ink tank (115). Still further, the data results received from testing the density of the ink solution (145) may be compared to previously measured or calculated data results for various pigment densities. If the data results are erroneous or non-congruent with the previously obtained data results the user may calibrate the optical density sensor (155) with the new data points. Additionally, if the data results indicate a more serious issue, the user may begin troubleshooting any mechanical or electrical issues with the optical density sensor (155).

The base oil tank (120) may contain a certain amount of base oil used in the ink solutions (140, 145) in order to build or create the first and second ink solutions (140, 145). Although in the present example FIG. 1 shows that the base oil tank (120) contains oil (150), many other types liquids or solids may be stored in the base oil tank (120) and used in creating an ink solution. Examples of additional materials that may be stored in the base oil tank (120) may include, but may not necessarily be limited to, solvents, dyes, resins, lubricants, solubilizers, surfactants, particulate matter, and fluorescers.

During factory assembly, the system (100), and more specifically the optical density sensor (155), may be calibrated. Specifically, a load cell (125) measures, by weight, an amount of pigment solids (135) added to the ink solution (140) within the intermediate dispersion unit (110). The load cell (125) is used to measure, by weight, an amount of pigment solids (135) to be added to an amount of oil (150) to achieve an ink solution (140,145) with an established pigment solid (135) density. In one example, the system may add an amount of pigment solids (135) to the oil (150) incrementally or all at once to achieve an ink solution (140, 145) with the established pigment solid (135) density. In yet another example, the system (100) may dilute an ink solution (140, 145) with an amount of oil (150) to achieve an ink solution (140, 145) with the established pigment solid (135) density.

Still further, in one example, the system (100) may provide an ink solution (140, 145) having a pigment solid (135) density set at a predetermined and specific set point. For example, the specific set point may be at or around 4.5% pigment solid (135) content. This set point may be chosen based on various external parameters.

When the ink solution (145) is returned to the ink tank (115), the optical density sensor (155) may measure the light intensity value (I) received at the photodetector (155) while at least a sample of the ink solution (145) is passed through the optical density sensor (155). Through the use of a processor (180), the optical density sensor (155) measurement is then correlated with the amount of pigment solids (135) added to the ink solution (145) at the predetermined set point. As will be discussed below, calibration of the optical density sensor (155) allows a user to add a certain amount of pigment solid (135) to a certain amount of oil (150) to achieve a desired pigment solid (135) density. The correlation between the amount of pigment solids (135) added to the oil and the light intensity (I) measurements taken by the optical density sensor (155) may be used to determine via the optical density sensor (155) the pigment solid (135) density.

Additionally, as will be discussed in more detail below, the gap between the lenses (165, 170) within the optical density sensor (155) may be determined after factory assembly. The entire system (100) is then calibrated such that the optical density sensor (155) accurately detects the pigment density of an ink originally measured by the load cell (125). In one example, this process may be repeated for various colored ink solutions (140, 145). In yet another example, the above process may be repeated with varying pigment solid (135) densities.

During operation, the optical density sensor (155) uses a light source (160) that transmits light through a number of lenses (165, 170) and ultimately to a photodetector (175). During testing of an ink solution, at least a sample of the ink is directed between the lenses (165, 170). The intensity of the light directed through the lenses (165, 170) is measured by the photodetector (175). The photodetector (175), when receiving light, may send signals to a processor (180) for interpretation and implementation such that data may be obtained as to the level of light intensity (I) received. Therefore, when a user is attempting to build an ink solution (145) having a specific pigment solid (135) density, the optical density sensor (155) may measure the light intensity (I) and the pigment solid (135) density of that specific ink solution (145) may be correlated with the measured intensity (I) value.

The relationship between the light intensity ($I_{meas}$) received at the photodetector and the density of the ink solution ($X_{meas}$) is defined as:

$$(I_{meas}-I_B)=(I_0-I_B)*\exp^{(-L*a*X_{meas})} \quad \text{(Eq. 1)}$$

where $I_{meas}$ is the light intensity measured at the photodetector when a sample of ink is sent through the optical density sensor (155); $X_{meas}$ is the pigment solid (135) density of the ink solution (140, 145) being measured; $I_B$ is the photodetector measurement with no laser transmission; $I_0$ is the measured intensity for a clear solution such as oil (150); L is the lens gap; and, a is a pigment characteristic that varies amongst pigment colors and can be calculated experimentally.

Because there may be an intrinsic shift in the electronic mode of the photodetector, $I_B$ is measured by taking a reading from the photodetector (175) when no light is being directed towards the photodetector (175). The electronic shift may come about as a consequence of general degradation of the various electrical wires and components within the photodetector (175), within the laser source, or combinations of these. Additionally, as mentioned above $I_0$ can be measured by passing a clear solution through the optical density sensor (155) and measuring the intensity value. The clear solution can be any clear solution that will produce an initial intensity value upon which to compare other intensity values measured with the optical density sensor (155). In one example, the clear solution is oil (150) and may be accessed by the optical density sensor (155) by pumping the oil (150) from the base oil tank (120) into the ink tank, and then pumped into the optical density sensor (155).

Since both $I_B$ and $I_0$ can be identified electronically, the calibration of the optical density sensor (155) at the factory may be done by solving the above equation (Eq. 1) for the lens gap L. This may be accomplished via the following formula:

$$L*a = \frac{1}{X_{meas}} * \ln\left[\frac{I_0 - I_B}{I_{meas} - I_B}\right] \quad \text{(Eq. 2)}$$

The distance between the lenses (165, 170), or the lens gap (L), is around a few hundred microns and, therefore, a small change in the lens gap (L) has an exponential effect on the pigment density measurements of the ink passing between the lenses (165, 170). As will be discussed later, later calculated values of L that do not match a factory calculated value of L may signify that the lens gap L has increased or decreased or that ink has coated on at least one of the lenses (165, 170).

Figure 2:
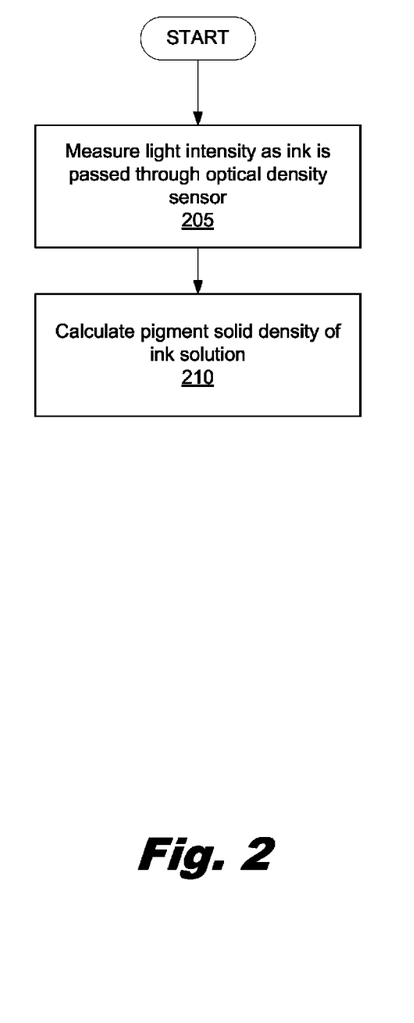
FIG. 2 is a flowchart depicting a method of measuring, dynamically, an ink solution comprising an undetermined pigment solid density according to one example of the principles described herein.

FIG. 2 is a flowchart depicting a method of measuring, dynamically, an ink solution comprising an undetermined pigment solid (135) density according to one example of the principles described herein. During use of the system (FIG. 1, 100) a user may need to build an ink solution (FIG. 1, 145) having a specific pigment solid (135) density. As the user adds pigment solids (FIG. 1, 135) to the oil (FIG. 150) the optical density sensor (FIG. 1, 150) may calculate the pigment solid (FIG. 1, 135) density of the ink solution (FIG. 1, 145) using Equation 1 above. The process begins with the optical density sensor (FIG. 1, 155) measuring (Block 205) the light intensity ($I_{meas}$) as the ink solution (FIG. 1, 145) is passed through the optical density sensor (FIG. 1, 155). In one example, a processor (FIG. 1, 180) may receive from the photodetector (FIG. 1, 175) the measured light intensity as the ink solution (FIG. 1, 145) is passed through the optical density sensor (FIG. 155). Using the factory determined values of $I_0$, $I_B$, L*a, and the newly measured intensity ($I_{meas}$), the pigment solid density ($X_{meas}$) may be readily calculated (Block 210).

Figure 3:
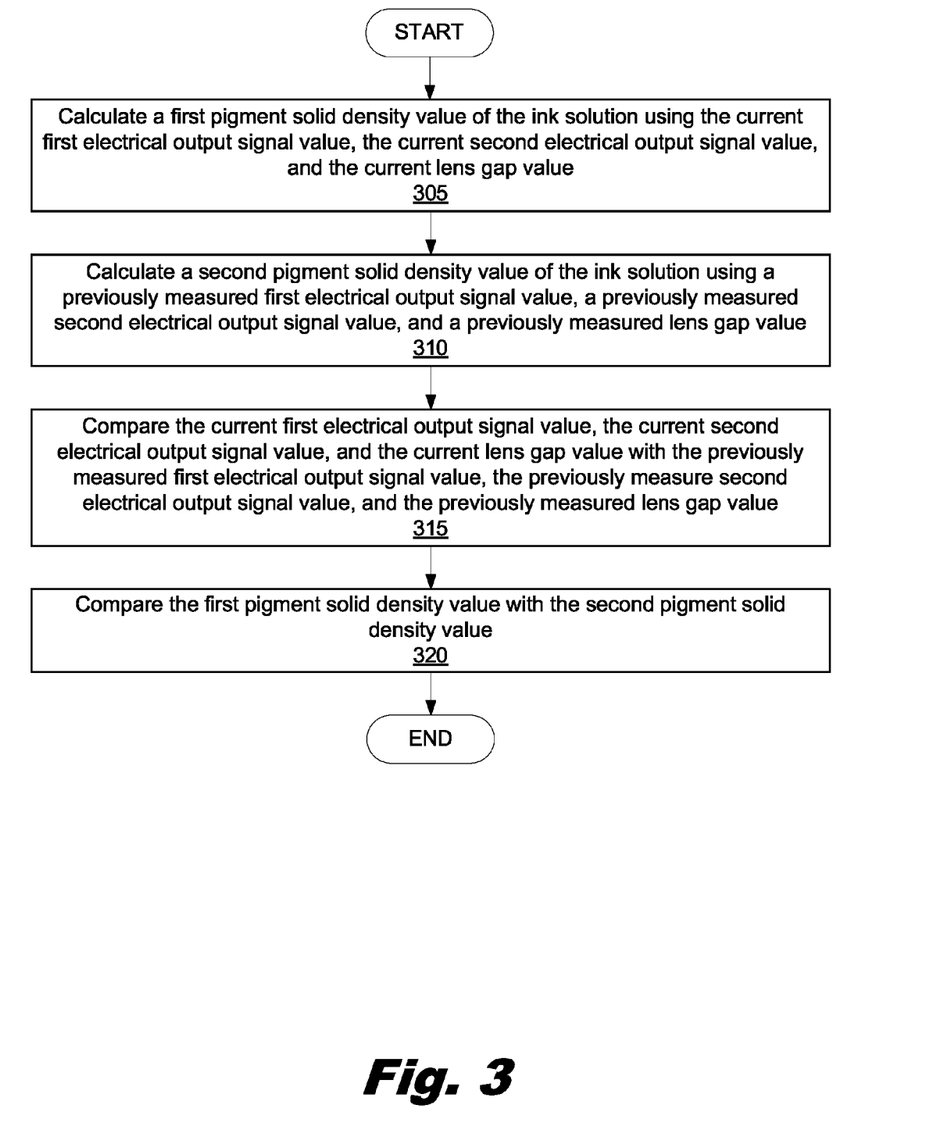
FIG. 3 is a flowchart depicting a method of diagnosing and calibrating an optical density sensor according to one example of the principles described herein.

Turning now to FIG. 3, a flowchart depicting a method of diagnosing and calibrating an optical density sensor according to one example of the principles described herein is shown. In calibrating and diagnosing an optical density sensor, the user may first calculate (Block 305, 310) the density values obtained in an ink building process with the calculated density values obtained during the factory calibration process or a previous calibration process. To accomplish this, the user, using equation 1 above, may solve for $X_{meas}$ at the set point. Therefore, the user may first calculate (Block 305) the density value of the ink solution at the set point using the current values of $I_0$, $I_B$, and L*a obtained during the calibration process. The user may then calculate (Block 310) the density value of the ink solution at the set point using the values of $I_0$, $I_B$, and L*a obtained during an earlier calibration process completed, for example, at the factory. In one example, the system (FIG. 1, 100) may calculate (Block 305, 310) the density values above for the user. To achieve this, the system (FIG. 1, 10) may include a processor (FIG. 1, 180) which receives the respective $I_0$, $I_B$, and L*a values and presents the solutions to the user via an output device.

The user then performs a direct comparison (Block 315) between the values of $I_0$, $I_B$, and L*a obtained during an earlier calibration process with the values of $I_0$, $I_B$, and L*a obtained during the current calibration process (Block 305 and 310). Here, the user may determine which values are not congruent and act accordingly.

Specifically, a value of $I_B$ obtained by the user's ink dilution or ink building process that is not congruent with the previously obtained value of $I_B$ may indicate that the photodetector (FIG. 1, 175) is not working properly. Upon an indication that the photodetector (FIG. 1, 175) is not working properly, the user may perform certain measures to fix or replace the photodetector (FIG. 1, 175) within the optical density sensor (FIG. 1, 155). However, if the difference in the value of $I_B$ from the factory calibration value and the value obtained during the user's ink dilution or ink building process are slightly off, this may indicate that the optical density sensor (FIG. 1, 155) may need to be recalibrated using the new value of $I_B$ obtained during the ink dilution or ink building process.

Additionally, a value of $I_0$ obtained by the user's ink dilution or ink building process may indicate a number of mechanical or electrical issues with the light source (FIG. 1, 160) or lenses (FIG. 1, 165, 170). For example, the light source (FIG. 1, 160) may not be emitting an appropriate amount of light and may need to be replaced. Additionally, the lenses (FIG. 1, 165, 170) may have a coating of sludge or other obstruction over them that would also produce erroneous results. Consequently, an extreme difference between the value of $I_0$ obtained during the user's ink building process and the value of $I_0$ obtained during the factory calibration process may indicate that parts of the optical density sensor (FIG. 1, 155) may need to be repaired or replaced.

However, if the difference in the value of $I_0$ from the factory calibration value and the value obtained during the user's ink building process are off, this may indicate that the optical density sensor (FIG. 1, 155) may need to be recalibrated using the new value of $I_0$ obtained during the ink dilution or ink building process.

Even further a different lens gap (FIG. 1, L) value may indicate that the lens gap (FIG. 1, L) has increased or decreased. As discussed earlier, a change in the lens gap (FIG. 1, L) will result in an exponential change in the pigment density values ($X_{meas}$) and may indicate that more serious actions will need to be taken.

After the user compares (Block 315) the values of $I_0$, $I_B$, and L*a obtained at the factory with the values of $I_0$, $I_B$, and L*a obtained during the current calibration process, the user may then compares (Block 320) the initial pigment density value obtained during an earlier calibration process with the current density value of the ink solution (FIG. 1, 145) obtained during the user's calibration process. Therefore, in one example the current set point density value at 4.5% pigment density may be compared with the factory set point density value at 4.5%. Because the density was measured and calculated by a load cell (FIG. 1, 125) during both the factory calibration and the user's subsequent calibration processes, a difference in pigment solid density from that obtained at the factory may indicate that the optical density sensor needs to be recalibrated, repaired, or replaced.

After the user has made these comparisons (Block 315, 320), the user may then decide how to adjust the optical density sensor if at all. Specifically, the user may determine whether the new values of $I_0$, $I_B$, L*a, and the pigment density warrant the recalibration of the optical density sensor (FIG. 1, 155) if at all. In one example there may be a predetermined threshold where the difference between one previously obtained value and the correlating value obtained during a user calibration process that will dictate whether the user adjusts certain parameters of the optical density sensor (FIG. 1, 155). For example, as discussed above, if the difference between $I_0$ obtained during the factory calibration and $I_0$ obtained during the user's calibration process is less than a predetermined threshold, the user may choose simply to do nothing and continue with the present settings of the optical density sensor (FIG. 1, 155).

If however, the difference between $I_0$ obtained during the factory calibration and $I_0$ obtained during the user's calibration process is more than a predetermined threshold, the user may choose to take appropriate action such as cleaning the lenses (FIG. 1, 165, 175) in the optical density sensor (FIG. 1, 155) or further investigate whether the light source (FIG. 1, 160) is working properly. Additionally, if the user sees that the difference between $I_0$ obtained during the factory calibration and $I_0$ obtained during the user's calibration process exceeds a second predetermined threshold, this may indicate that more serious actions need to done to repair or replace all or parts of the optical density sensor (FIG. 1, 155).

The similar process described above may be conducted with each of the values used to calibrate the optical density sensor (FIG. 1, 155). Specifically, the values of I0, IB, L*a, and the calculated pigment density obtained in the user's calibration may each be compared to the same values obtained during the previous calibration process and the user may decide whether to update the optical density sensor with those new calibration values. Again, if any one of these values differ from their respective previously obtained value by a predetermined threshold, the user may initiate a troubleshooting procedure to fix or replace the optical density sensor (FIG. 1, 155). As discussed above, a processor (FIG. 1, 180) may assist the user in determining what to do via a troubleshooting procedure. Therefore, the processor may receive instructions and data sufficient to direct the user on how to best adjust, repair, or replace the optical density sensor (FIG. 1, 155). The processor may accomplish this through the use of a user interface (FIG. 1, 185).

Figure 4:
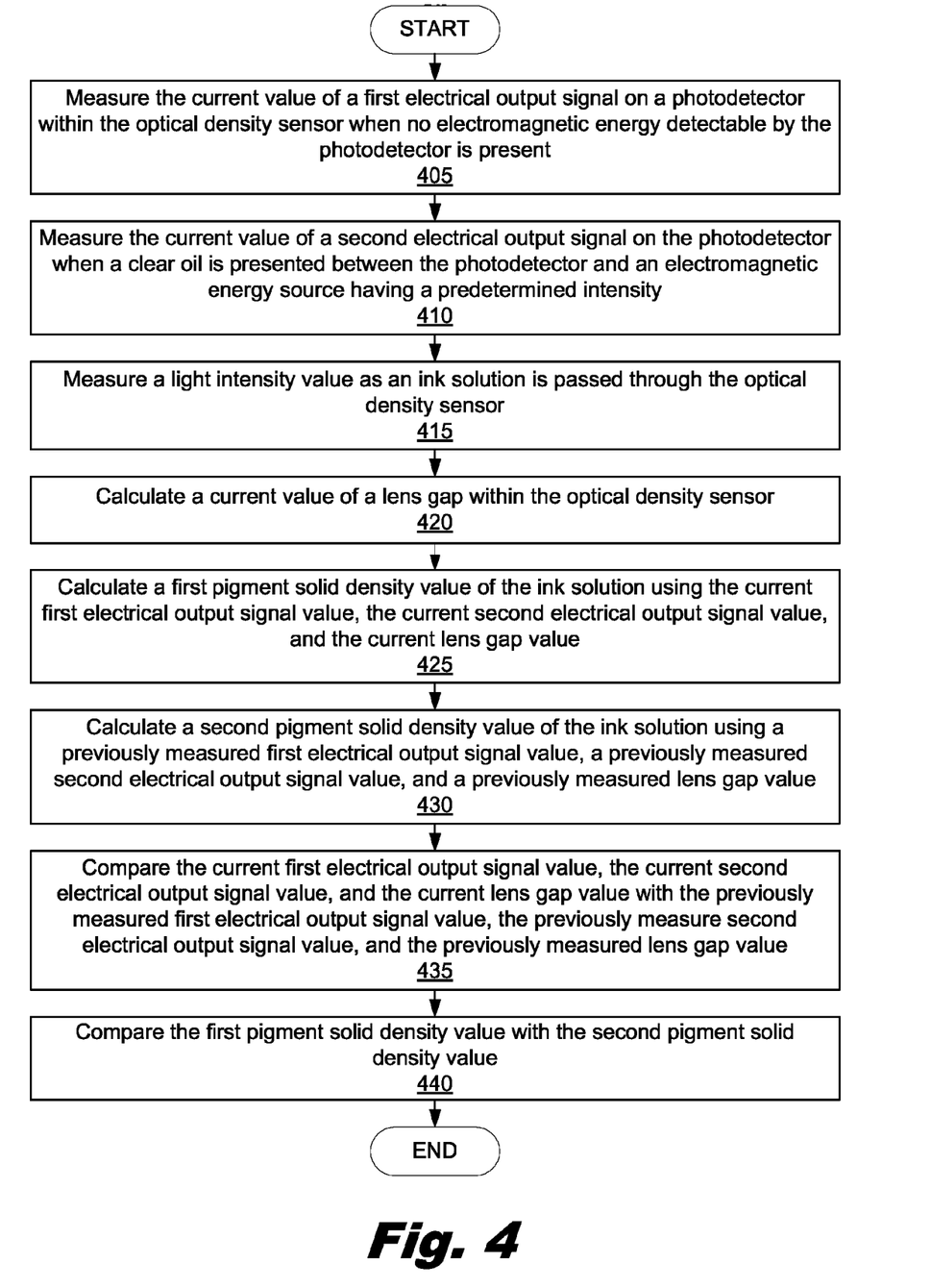
FIG. 4 is a flowchart depicting another method of diagnosing and calibrating an optical density sensor according to one example of the principles described herein.

FIG. 4 is a flowchart depicting another method of calibrating an optical density sensor (FIG. 1, 155), according to one example of the principles described herein. As discussed previously, before a user attempts to calibrate the optical density sensor (FIG. 1, 155), measurements and calculations may be initially made at the factory to determine the values of the variables described in connection with the equation (Eq. 1). Specifically, at the factory the values for $I_B$ and $I_0$ are determined as described above. Therefore, $I_B$ may be measured by taking a reading from the photodetector (FIG. 1, 175) when no light is being directed towards the photodetector (FIGS. 1, 175) and $I_0$ may be measured by passing a clear solution through the optical density sensor (FIG. 1, 155) and measuring the intensity value.

Additionally, the value $X_{meas}$ may be determined before an ink is used in the calibration process at the factory and, therefore, in this initial calibration, the density value of the ink used is established through the use of the load cell (FIG. 1, 125). Consequently, a specific ink having an established pigment solid density may be used to first calibrate the optical density sensor (155) at the factory. With these variables, and with the measured intensity ($I_{meas}$) results, the above equation (Eq. 1) may be solved for L*a. Since a is an established constant based on the light absorption properties of the ink used during calibration, L may be determined. The initial factory calibration process may then be repeated with a number of different colored ink solutions and with ink solutions having a varying and established pigment solid (FIG. 1, 135) density.

When the optical density sensor (FIG. 1, 155) is calibrated by a user, the user may first measuring (Block 405, 410) the current value of a first electrical output signal on a photodetector within the optical density sensor when no electromagnetic energy detectable by the photodetector is present ($I_B$) and the current value of a second electrical output signal on the photodetector when a clear oil is presented between the photodetector and an electromagnetic energy source having a predetermined intensity ($I_0$). To measure $I_B$ (Block 405) the user would take a reading from the photodetector (FIG. 1, 175) when no light is being directed towards the photodetector (FIG. 1, 175). The value of $I_B$ may vary due to an electronic shift of the electronic mode of the photodetector (FIG. 1, 175) as the optical density sensor (FIG. 1, 155) is used by the user. As will be discussed later, this value will then be compared (Block 430) to the $I_B$ value measured at the factory. A difference in value from that measured at the factory may reveal that the photodetector (FIG. 1, 175) is not working properly. In one example, the user may be notified by the system (FIG. 1, 100) that the photodetector (FIG. 1, 175) is not working properly and may be directed to perform various actions to fix or replace the photodetector (FIG. 1, 175) within the optical density sensor (FIG. 1, 155). The user may be notified via user interface.

The user also measures (Block 410) the value of $I_0$. The user measures (Block 410) this value by measuring the light intensity (I) value of light passing through a clear solution, such as oil (FIG. 1, 150), when it is passed through the optical density sensor (FIG. 1, 155). Again, as will be discussed below, a change in this value would indicate a number of mechanical or electrical issues with the light source (FIG. 1, 160) or lenses (FIG. 1, 165, 170). For example, the light source (FIG. 1, 160) may not be emitting an appropriate amount of light and may need to be replaced. Additionally, the lenses (FIG. 1, 165, 170) may have a coating of sludge or other obstruction over them that would also produce erroneous results.

In one example, after $I_0$ and $I_B$ have been measured (Block 405, 410), a user may begin to build an ink solution (FIG. 1, 135). As briefly discussed above, this is accomplished using an ink calibration can (FIG. 1, 105), an intermediate dispersion unit (FIG. 1, 110), an ink tank (FIG. 1, 115), a base oil tank (FIG. 1, 120), and a load cell (FIG. 1, 125). In one example, the ink solution (FIG. 1, 145) may be built by incrementally adding an amount of pigment solids (FIG. 1, 135) to an amount of oil (FIG. 1, 150) or adding an amount of pigment solids (FIG. 1, 135) to an amount of ink solution (FIG. 1, 140, 145). As each amount of pigment solids (FIG. 135) are added to the oil (FIG. 1, 150), the load cell (FIG. 1, 125) measures the weight of the pigment solids (FIG. 1, 125). Through a calculation, the pigment solid density of the ink solution (FIG. 1, 145) can then be determined. Indeed, because the load cell (FIG. 1, 125) weighs the pigment solids (FIG. 1, 135) within an accuracy of ±2 grams, the accuracy of the pigment solid density calculations varies by around ±0.03%. After an amount of pigment solids (FIG. 1, 135) is added to an amount of oil (FIG. 1, 150) in the intermediate dispersion unit (FIG. 1, 110), the ink solution (FIG. 1, 145) is then pumped into an ink tank (FIG. 1, 115).

In another example, at least a portion of that pigment solid (FIG. 1, 135) and oil (FIG. 1, 150) solution may be pumped it into a intermediate dispersion unit (FIG. 1, 110) and an additional amount of pigment solids (FIG. 1, 135) is added to the pigment solid (FIG. 1, 135) and oil (FIG. 1, 150) solution. Again, the amount of pigment solid (FIG. 1, 135) added to the oil (FIG. 1, 150) may be an exact amount that produce a certain pigment solid (FIG. 1, 135) density within the ink solution (FIG. 1, 140, 145). In this example, the process is repeated, incrementally adding an amount of pigment solids (FIG. 1, 135) to an ink solution (FIG. 1, 140, 145) with a calculated pigment solid density, until a predetermined pigment solid (FIG. 1, 135) density has been achieved within the ink solution (FIG. 1, 140). To achieve this, the ink tank (FIG. 1, 115) may be a source from which the intermediate dispersion unit (FIG. 1, 110) receives at least a portion of the ink solution (FIG. 1, 145) being built. The ink calibration can (FIG. 1, 105) may then add an additional amount of pigment solids (FIG. 1, 135) incrementally to increase the pigment solid (FIG. 1, 135) density of the ink solution (FIG. 1, 145) until a desired pigment solid (FIG. 1, 135) density is reached. In one example, the desired pigment solid (FIG. 1, 135) density to be reached may be a predetermined set point as will be discussed later.

As discussed above, each time an additional amount of pigment solids (FIG. 1, 135) is added to the ink solution (FIG. 1, 145), the ink solution may be pumped back into the ink tank (FIG. 1, 115). During each iteration, the optical density sensor (FIG. 1, 155) then measures (Block 415) the transferred light intensity ($I_{meas}$) value as the ink solution (FIG. 1, 145) is passed through the optical density sensor (155) and between laser source and the photodetector. The optical density sensor may measure the light intensity ($I_{meas}$) value during each iteration until a pigment density is reached that is substantially equal to a predetermined set point. As will be discussed later, the light intensity ($I_{meas}$) value measured at this set point will be compared to the light intensity ($I_{meas}$) value measured at the same set point during an earlier factory calibration procedure. The difference between the measured values will then help determine what action the user is to take in repairing or replacing the optical density sensor (FIG. 1, 155).

In another example, instead of an ink solution (FIG. 1, 140, 145) being built, an ink solution having an established pigment solid (FIG. 1, 135) density may be diluted incrementally to achieve a desired pigment solid (FIG. 1, 135) density. In this example, the system (FIG. 1, 100) may be used to add additional amounts of oil (FIG. 1, 150) to the ink solution incrementally until the calculation by the load cell indicate that the desired pigment solid (FIG. 1, 135) density has been reached.

In yet another example, an ink having an established pigment solid density may be used. In this example, instead of building an ink solution, a user may calibrate the optical density sensor (FIG. 1, 155) by using an ink solution with an already established pigment solid density.

After the ink building process has concluded, a light intensity ($I_{meas}$) measurement of the ink solution may been taken (Block 415) using the optical density sensor (FIG. 1, 155). The user then calculates (Block 420) the lens gap (FIG. 1, L) using the values of $I_B$, $I_0$, and $I_{meas}$ obtained (Block 405 and 415) by the user during the ink building process. In one example, the value of $I_{meas}$ may be from a specific set point. To accomplish this, the user may use Equation 2 above, solving for L*a. Again, because a is a pigment characteristic that can be calculated experimentally and is determined in advance, the user may be able to solve for the lens gap (FIG. 1, L).

In another example, the system (FIG. 1, 100) may calculate (Block 420) L*a for the user. Specifically, the system may incorporate a processor (FIG. 1, 180) that receives the values of $I_B$ and $I_0$ obtained after the ink building process and, using the equation above (Eq. 2), calculates L.

After the value of L*a has been calculated (Block 420), the user may calculate (Block 425, 430) the density values obtained in the user's ink building process with the calculated density values obtained during the factory calibration process or a previous calibration process. To accomplish this, the user, using equation 1 above, may solve for $X_{meas}$ at the set point. Therefore, the user may first calculate (Block 425) the density value of the ink solution at the set point using the initial values of $I_0$, $I_B$, and L*a obtained at the factory. The user may then calculate (Block 430) the density value of the ink solution at the set point using the current values of $I_0$, $I_B$, and L*a obtained during this calibration process (Block 405, 410, and 420). In one example, the system (FIG. 1, 100) may calculate (Block 425, 430) the density values above for the user. To achieve this, the system (FIG. 1, 10) may include a processor (FIG. 1, 180) which receives these values and presents the solutions to the user via an output device.

The user then performs a direct comparison (Block 430) between the values of $I_0$, $I_B$, and L*a obtained at the factory with the values of $I_0$, $I_B$, and L*a obtained during the current calibration process (Block 405 and 420). Here, the user may determine which values are not congruent and act accordingly.

As discussed above, a value of $I_B$ obtained by the user's ink dilution or ink building process that is not congruent with the factory obtained value of $I_B$ may indicate that the photodetector (FIG. 1, 175) is not working properly. Upon an indication that the photodetector (FIG. 1, 175) is not working properly, the user may perform certain measures to fix or replace the photodetector (FIG. 1, 175) within the optical density sensor (FIG. 1, 155). However, if the difference in the value of $I_B$ from the factory calibration value and the value obtained during the user's ink dilution or ink building process are slightly off, this may indicate that the optical density sensor (FIG. 1, 155) may need to be recalibrated using the new value of $I_B$ obtained during the ink dilution or ink building process.

Additionally, a value of $I_0$ obtained by the user's ink dilution or ink building process may indicate a number of mechanical or electrical issues with the light source (FIG. 1, 160) or lenses (FIG. 1, 165, 170). For example, the light source (FIG. 1, 160) may not be emitting an appropriate amount of light and may need to be replaced. Additionally, the lenses (FIG. 1, 165, 170) may have a coating of sludge or other obstruction over them that would also produce erroneous results. Consequently, an extreme difference between the value of $I_0$ obtained during the user's ink building process and the value of $I_0$ obtained during the factory calibration process may indicate that parts of the optical density sensor (FIG. 1, 155) may need to be repaired or replaced.

However, if the difference in the value of $I_0$ from the factory calibration value and the value obtained during the user's ink building process are off, this may indicate that the optical density sensor (FIG. 1, 155) may need to be recalibrated using the new value of $I_0$ obtained during the ink dilution or ink building process.

Even further a different lens gap (FIG. 1, L) value may indicate that the lens gap (FIG. 1, L) has increased or decreased. As discussed earlier, a change in the lens gap (FIG. 1, L) will result in an exponential change in the pigment density values ($X_{meas}$) and may indicate that more serious actions will need to be taken.

After the user compares (Block 435) the values of $I_0$, $I_B$, and L*a obtained at the factory with the values of $I_0$, $I_B$, and L*a obtained during the current calibration process (Block 405 and 420), the user may then compare (Block 440) the initial pigment density value obtained at the factory with the current density value of the ink solution (FIG. 1, 145) obtained during the user's calibration process. Therefore, in one example the current set point density value at 4.5% pigment density may be compared with the factory set point density value at 4.5%. Because the density was measured and calculated by a load cell (FIG. 1, 125) during both the factory calibration and the user's subsequent calibration processes, a difference in pigment solid density from that obtained at the factory may indicate that the optical density sensor needs to be recalibrated, repaired, or replaced.

After the user has compared (Block 435) the values of $I_0$, $I_B$, and L*a obtained at the factory with the values of $I_0$, $I_B$, and L*a obtained during the current calibration process and compared (Block 440) the initial pigment density value obtained at the factory with the current density value of the ink solution (FIG. 1, 145) obtained during the user's calibration process, the user may then decide how to adjust the optical density sensor if at all. Specifically, the user may determine whether the new values of $I_0$, $I_B$, L*a, and the pigment density warrant the recalibration of the optical density sensor (FIG. 155) if at all. In one example there may be a predetermined threshold where the difference between one factory obtained value and the correlating value obtained during a user calibration process that will dictate whether the user adjusts certain parameters of the optical density sensor (FIG. 1, 155). For example, as discussed above, if the difference between $I_0$ obtained during the factory calibration and $I_0$ obtained during the user's calibration process is less than a predetermined threshold, the user may choose simply to do nothing and continue with the present settings of the optical density sensor (FIG. 1, 155).

If however, the difference between $I_0$ obtained during the factory calibration and $I_0$ obtained during the user's calibration process is more than a predetermined threshold, the user may choose to take appropriate action such as cleaning the lenses (FIG. 1, 165, 175) in the optical density sensor (FIG. 1, 155) or further investigating whether the light source (FIG. 1, 160) is working properly. Additionally, if the user sees that the difference between $I_0$ obtained during the factory calibration and $I_0$ obtained during the user's calibration process exceeds a second predetermined threshold, this may indicate that more serious actions need to done to repair or replace all or parts of the optical density sensor (FIG. 1, 155).

The similar process described above may be conducted with each of the values used to calibrate the optical density sensor (FIG. 1, 155). Specifically, the values of I0, IB, L*a, and the calculated pigment density obtained in the user's calibration may each be compared to the same values obtained during the factory calibration process and the user may decide whether to update the optical density sensor with those new calibration values. Again, if any one of these values differ from their factory obtained value by a predetermined threshold, the user may initiate a troubleshooting procedure to fix or replace the optical density sensor (FIG. 1, 155). As discussed above, a processor (FIG. 1, 180) may assist the user in determining what to do via a troubleshooting procedure. Therefore, the processor may receive instructions and data sufficient to direct the user on how to best adjust, repair, or replace the optical density sensor (FIG. 1, 155). The processor may accomplish this through a user interface (FIG. 1, 185).

Still further, the calibration process described above may be conducted using multiple intensity ($I_{meas}$) readings (Block 415) for various ink solutions (FIG. 1, 140, 145) having different pigment solid densities. The multiple intensity ($I_{meas}$) readings (Block 415) may be obtained during the ink building process mentioned above. These additional measured (Block 415) points may be used to analyze and estimate the stability and correctness of the current measurements taken during the calibration process. Further, these measurements may be taken into consideration in deciding how to adjust the operating parameters of the optical density sensor (FIG. 1, 155).

Figure 5:
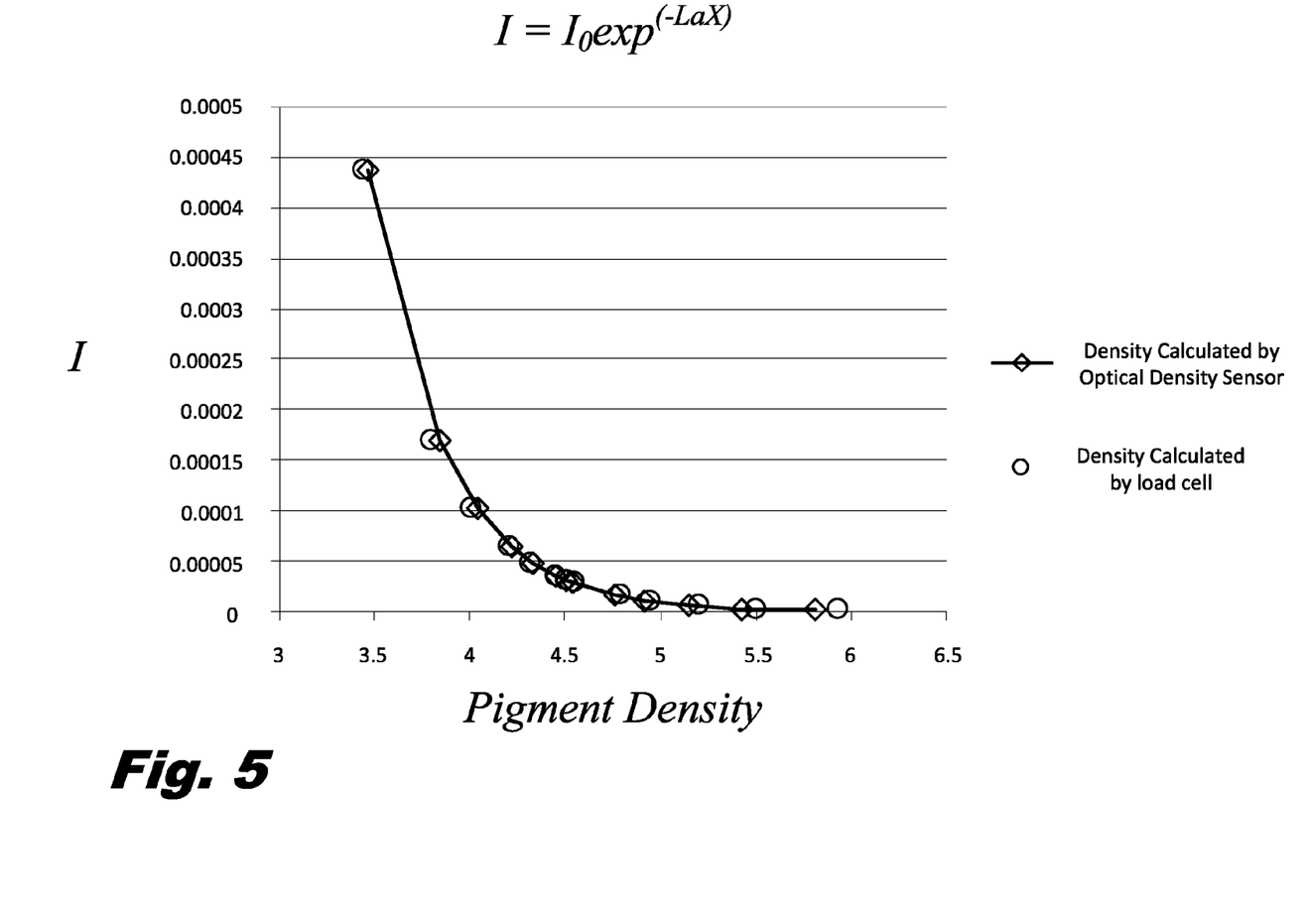
FIG. 5 is a graph indicating the light intensity values versus the pigment densities of an ink solution for a number of pigment densities according to one example of principles described herein.

FIG. 5 shows a graph indicating the light intensity values versus the pigment densities of an ink solution (FIG. 1, 140, 145) for a number of pigment densities according to one example of principles described herein. The data points presented in the graph of FIG. 5 are examples of data points that were measured and calculated during an ink building process, and other data points may be obtained if the ink building process were performed a subsequent time. In this specific example, an ink solution was built via a load cell (FIG. 1, 125) with almost 6% (5.932%) of NVS (non-evaporated solids) and diluted with measured amounts of oil the solution by using the load cell (FIG. 1, 125). The solution was diluted up to 3.441% of NVS (non-evaporated solids).

In FIG. 5, a diamond is used to plot the values calculated through an light intensity (I) value taken by an optical density sensor (FIG. 1, 155) throughout a range of pigment solid (FIG. 1, 135) densities. A circle is used to plot the density values of an ink solution throughout a range of pigment solid (FIG. 1, 135) densities values, the values calculated through the use of a load cell (FIG. 1, 125). The following table indicates the specific values of each data point (DP) plotted.

TABLE 1

|                  | DP 1        | DP 2        | DP 3        | DP 4        |
|------------------|-------------|-------------|-------------|-------------|
| % NVS (Load Cell) | 5.932       | 5.504       | 5.202       | 4.949       |
| Measured I       | 1.0713E−06  | 2.90227E−06 | 5.88707E−06 | 1.08011E−05 |
| % NVS (ODS)      | 5.81261704  | 5.424376114 | 5.148843052 | 4.912415048 |
| Difference       | −0.119      | −0.079      | −0.053      | −0.036      |

|                  | DP 5        | DP 6        | DP 7        | DP 8        |
|------------------|-------------|-------------|-------------|-------------|
| % NVS (Load Cell) | 4.798       | 4.555       | 4.501       | 4.451       |
| Measured I       | 1.61155E−05 | 2.83095E−05 | 3.10533E−05 | 3.56987E−05 |
| % NVS (ODS)      | 4.75653263  | 4.53703955  | 4.501       | 4.446690459 |
| Difference       | −0.042      | −0.018      | 0.000       | −0.004      |

|                  | DP 9        | DP 10       | DP 11       | DP 12       |
|------------------|-------------|-------------|-------------|-------------|
| % NVS (Load Cell) | 4.324       | 4.209       | 4.012       | 3.803       |
| Measured I       | 4.83659E−05 | 6.4455E−05  | 0.000101983 | 0.000169687 |
| % NVS (ODS)      | 4.328383945 | 4.21651056  | 4.037756162 | 3.839404388 |
| Difference       | 0.005       | 0.007       | 0.026       | 0.037       |

|                  | DP 13       |
|------------------|-------------|
| % NVS (Load Cell) | 3.441       |
| Measured I       | 0.000437704 |
| % NVS (ODS)      | 3.470248259 |
| Difference       | 0.029       |

Table 1 shows a number of data points (DP) that are reflected in FIG. 5. Each data point has a % NVS (Load Cell) value (% non-evaporated solids; load cell), a Measured I value, a % NVS (ODS) value (% non-evaporated solids; optical density sensor), and a calculated difference value. The % NVS (Load Cell) values were obtained from the load cell (FIG. 1, 125) as described above. Therefore, during the factory calibration process, the load cell measures the amount of pigment within an ink solution (FIG. 1, 140, 145). This is done by measuring the weight of the pigment solid (FIG. 1, 135) added to the ink solution (FIG. 1, 140, 145) and calculating the pigment solid density as the pigment solid (FIG. 1, 135) is added to an amount of oil (FIG. 1, 150). Because of the high precision of the load cell (±2 grams) the load cell (FIG. 1, 125) may provide an ink solution (FIG. 1, 140, 145) that has an accurate pigment solid (FIG. 1, 135) density.

Data point 7 (DP 7) in table 1 has been set as the set point from which all other data points are made and plotted in the graph shown in FIG. 5. With reference specifically to data point 7 in table 1, it can be seen that the % NVS (ODS) value is the same as that obtained by the load cell (FIG. 1, 125).

However, unlike any previous solutions, the measured difference between the % NVS (ODS) value and the % NVS (Load Cell) value is quite small over longer ranges of pigment solid (FIG. 1, 135) densities. Indeed, referring the set point as 100%, an inaccuracy of 0.4% is seen with a 2% difference in pigment solid (FIG. 1, 135) density. Moving even further from the set point to 33% pigment solid (FIG. 1, 135) density, a 2% difference is realized using this process. The deviations between the % NVS (ODS) value and the % NVS (Load Cell) value therefore may indicate the threshold level at which the optical density sensor (FIG. 155) is recalibrated or not. For example, if the difference between % NVS (ODS) value and the % NVS (Load Cell) for an ink solution similar to that shown in data point 5 is smaller than −0.042, then that may indicate that the optical density sensor is working within a predefined tolerance. If, however, the difference exceeds the −0.042 value, that may indicate that either the optical density sensor needs to be updated with the newly obtained $I_0$, $I_B$, and L*a values or that a troubleshooting procedure may need to be initiated.

Figure 6:
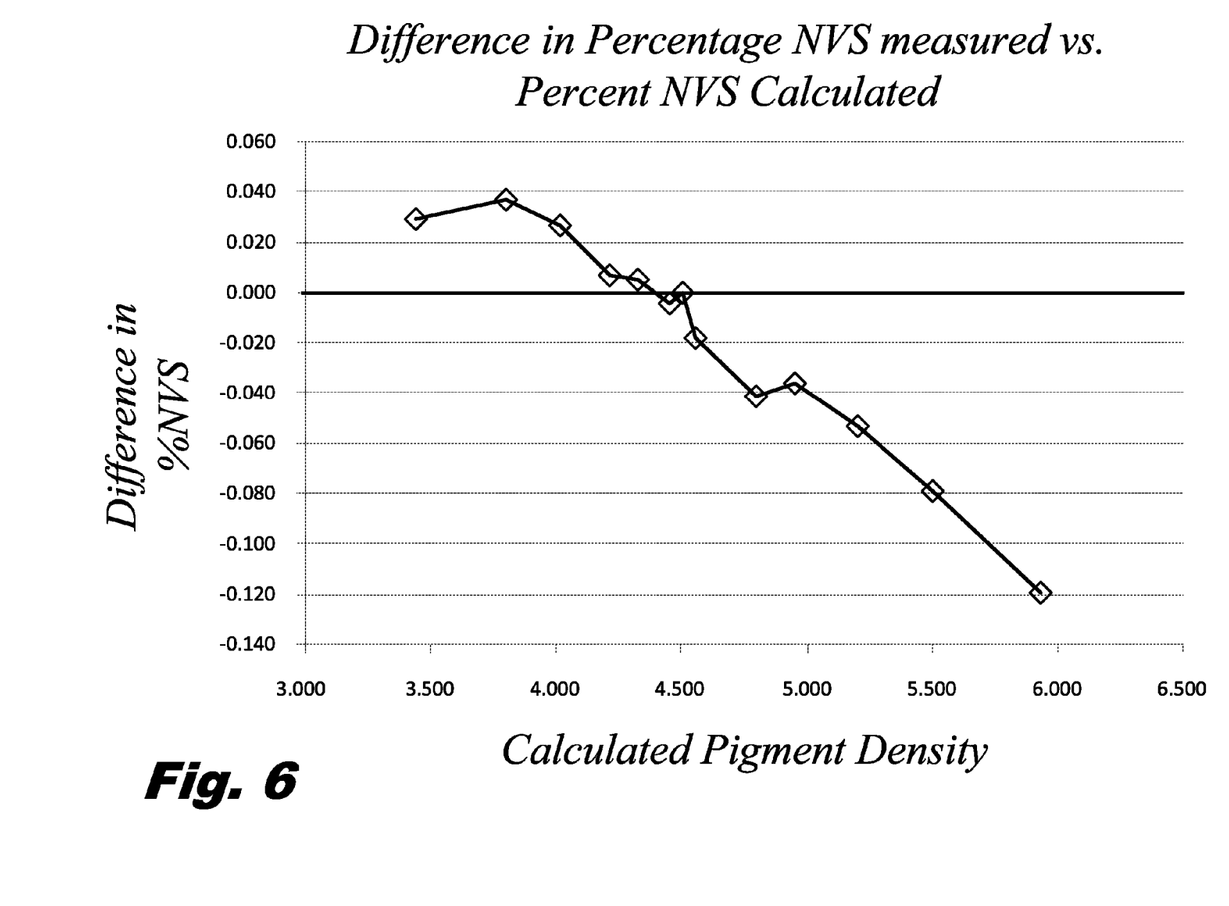
FIG. 6 is a graph indicating the difference in the ink density values obtained from the load cell and the optical density sensor according to one example of principles described herein.

FIG. 6 shows this relatively small pigment density deviation in a form of a graph that is indicating the difference in the ink density values obtained from the load cell (FIG. 1, 125) and the optical density sensor (FIG. 1, 155) according to one example of principles described herein. Again, as can be seen in FIG. 6, the inaccuracy, although increasing over the range, is relatively small compared to the inaccuracies obtained using a generally applicable look-up table calibration process. It is this small inaccuracy over a large range which, in part, allows the user to determine whether to recalibrate the optical density sensor (FIG. 1, 155) or repair or replace parts of the optical density sensor (FIG. 1, 155).

As previously discussed above in connection with FIG. 4, after measuring the values of $I_0$ and $I_B$, (FIG. 4, Block 405, 410), calculating L (FIG. 4, Block 420), and comparing these calculations with those done during the factory calibration process (FIG. 4, Block 435) the user may decide, based on the results, to recalibrate the optical density sensor (FIG. 1, 155) with the new $I_0$, $I_B$, and L values. When this is done, the optical density sensor (FIG. 1, 155) is updated with these values and any subsequent ink building process can be done with similarly accurate pigment solid density values as those shown in Table 1 and FIGS. 4 and 5.

However, if the values for $I_0$, $I_B$, and L are off by more than a predetermined threshold, the user may begin to troubleshoot any issues that might be present with the optical density sensor (FIG. 1, 155). In order to achieve this, the system (FIG. 1, 100) may further include a processor (FIG. 1, 180) and a user interface (FIG. 1, 185). With the processor (FIG. 1, 180), the user may interact, through the user interface (FIG. 1, 185), with a troubleshooting program. The troubleshooting program may direct the user to perform specific tasks in order to correct any perceived issues. Specifically, because the values for $I_0$, $I_B$, and L are off by more than the predetermined threshold this may be indicative of the fact that there is sludge over the lenses (FIG. 1, 165, 170), the photodetector (FIG. 1, 175) is defective, the light source (FIG. 1, 160) is defective, or that the gap (L) between the lenses (FIG. 1, 165, 170) has increased or decreased. These issues may be addressed in order to properly fix and then calibrate the optical density sensor (FIG. 1, 155).

The specification and figures describe a process for calibrating and troubleshooting an optical density sensor. The process includes, at the factory, calibrating the optical density sensor via the use of a load cell and, during a subsequent calibration process, calibrating the optical density sensor based on any new values for $I_0$, $I_B$, or L in Equation 1 above. The process allows for inks have a more accurate pigment density as well as the ability to build an ink solution having a specific pigment solid density with the optical density sensor. Additionally, the process allows a user to readily determine whether the optical density needs to be calibrated at all and whether a troubleshooting process needs to be initiated to determine what parts of the optical density sensor needs to be repaired or replaced.

The preceding description has been presented only to illustrate and describe examples of the principles described. This description is not intended to be exhaustive or to limit these principles to any precise form disclosed. Many modifications and variations are possible in light of the above teaching.

What is claimed is:

1. A system for calibrating an optical density sensor, comprising:
    an ink calibration can containing an amount of pigment solids;
    an intermediate dispersion unit fluidly coupled to the ink calibration can;
    a load cell engaged with the intermediate dispersion unit that measures a weight of pigment solids being deposited into the intermediate dispersion unit;
    an ink tank fluidly coupled to the intermediate dispersion unit;
    a base oil tank containing an amount of oil and fluidly coupled to the ink tank; and
    an optical density sensor fluidly coupled to the ink tank.

2. The system of claim 1, in which
    the intermediate dispersion unit:
        receives an amount of pigment solids from the ink calibration can; and
        receives an amount of oil from the base oil tank;
    the load cell weighs the amount of pigment solids received by the intermediate dispersion unit;
    the optical density sensor measures the light intensity value of the pigment solid and oil mixture; and
    a correlation between the weight of pigment solids added and the measured light intensity value is made.

3. The system of claim 2, in which the correlation between the weight of pigment solids added and the measured light intensity value is expressed by a formula whose parameters are measured and calculated during calibration.

4. The system of claim 1, in which the optical density sensor further comprises:
    an electromagnetic source;
    a photodetector in optical communication with the electromagnetic source; and
    a number of lenses optically coupling the electromagnetic source to the photodetector.

5. The system of claim 4, in which:
    a first electrical output signal on the photodetector is measured when no electromagnetic energy is directed towards the photodetector;
    a second electrical output signal of the photodetector is measured when a clear oil is presented between the photodetector and an electromagnetic source with a predetermined intensity; and
    a lens gap within the optical density sensor is calculated.

6. The system of claim 5, in which the optical density sensor is recalibrated if the difference between the lens gap and a lens gap value obtained during a previous optical density sensor calibration process is below a predetermined threshold.

7. The system of claim 5, in which a troubleshooting procedure is initiated if the difference between the lens gap and a lens gap value obtained during a previous optical density sensor calibration process is below a predetermined threshold.

8. The system of claim 1, further comprising a pump fluidly coupling the ink tank to the intermediate dispersion unit in which the pump pumps an amount of ink solution from the ink tank to the intermediate dispersion unit and in which the pigment solid density of the ink solution within the ink tank is established.

9. A method of calibrating the system of claim 1, the method comprising calibrating said optical density sensor by:
    calculating a first pigment solid density value of an ink solution using a current first electrical output signal value from a photodetector, a current second electrical output signal value from a photodetector, and a current lens gap value;

calculating a second pigment solid density value of the ink solution using a previously measured first electrical output signal value, a previously measured second electrical output signal value, and a previously measured lens gap value;

comparing the current first electrical output signal value, the current second electrical output signal value, and the current lens gap value with the previously measured first electrical output signal value, the previously measure second electrical output signal value, and the previously measured lens gap value; and comparing the first pigment solid density value with the second pigment solid density value.

10. The method of claim 9 further comprising:

obtaining the current first electrical output signal value by measuring an electrical output signal on a photodetector within the optical density sensor when no electromagnetic energy detectable by the photodetector is present; and obtaining the current second electrical output signal value by measuring an electrical output signal on a photodetector within the optical density sensor when a clear oil is presented between the photodetector and an electromagnetic energy source having a predetermined intensity.

11. A method of claim 9 further comprising recalibrating the optical density sensor if a difference between the current first electrical output signal value and the previously measured first electrical output signal value is below a predetermined threshold.

12. The method of claim 9, further comprising initiating a troubleshooting procedure if a difference between the current first electrical output signal value and the previously measured first electrical output signal value is above a predetermined threshold.

13. The method of claim 9, further comprising recalibrating the optical density sensor if a difference between the current second electrical output signal value and the previously measured second electrical output signal value is below a predetermined threshold.

14. The method of claim 9, further comprising initiating a troubleshooting procedure if a difference between the current second electrical output signal value and the previously measured second electrical output signal value is above a predetermined threshold.

15. The method of claim 9, further comprising recalibrating the optical density sensor if a difference between the current lens gap value and previously measured lens gap value is below a predetermined threshold.

16. The method of claim 9, further comprising initiating a troubleshooting procedure if a difference between the current lens gap value and previously measured lens gap value is above a predetermined threshold.

17. The method of claim 9, in which the previously measured lens gap value is obtained through formula parameters specific to the optical density sensor.

18. The method of claim 9, further comprising recalibrating the optical density sensor if a difference between the first pigment solid density value and the second pigment solid density value is below a predetermined threshold.

19. The method of claim 9, further comprising initiating a troubleshooting procedure if a difference between the first pigment solid density value and the second pigment solid density value is above a predetermined threshold.

20. A method of self-fixing and troubleshooting the system of claim 1, the method comprising calibrating said optical density sensor during a calibration process by:

measuring a first electrical output signal on a photodetector within the optical density sensor when no light is directed towards the photodetector, measuring a second electrical output signal on the photodetector when a clear oil is presented between the photodetector and a light source having a predetermined intensity;

building an ink solution by adding incremental amounts of pigment solids to an oil;

with the optical density sensor, measuring a light intensity value as the ink solution is passed through the optical density sensor at a predetermined set point;

calculating a lens gap within the optical density sensor; and comparing the lens gap value with a lens gap value obtained during a previous optical density sensor calibration process recalibrating the optical density sensor based on the first electrical output value, the second electrical output value, and the lens gap value.

* * * * *

UNITED STATES PATENT AND TRADEMARK OFFICE
CERTIFICATE OF CORRECTION

| | | |
|---|---|---|
| PATENT NO. | : 8,922,777 B2 | |
| APPLICATION NO. | : 13/160088 | |
| DATED | : December 30, 2014 | |
| INVENTOR(S) | : Zvi Shemer et al. | |

It is certified that error appears in the above-identified patent and that said Letters Patent is hereby corrected as shown below:

On the title page, Primary Examiner, in column 2, line 1, delete "Kara A Geisel" and insert -- Kara E Geisel --, therefor.

In the claims

In column 17, line 29, in Claim 11, delete "A" and insert -- The --, therefor.

Signed and Sealed this
Fourteenth Day of June, 2016

Michelle K. Lee
*Director of the United States Patent and Trademark Office*